US008936936B2

(12) United States Patent
Holmes et al.

(10) Patent No.: US 8,936,936 B2
(45) Date of Patent: Jan. 20, 2015

(54) METHODS AND COMPOSITIONS FOR TARGETED INTEGRATION

(75) Inventors: Michael C. Holmes, Oakland, CA (US); Shuyuan Yao, San Diego, CA (US); Luigi Naldini, Pioltello (IT); Angelo Leone Lombardo, Sangano (IT)

(73) Assignees: Sangamo BioSciences, Inc., Richmond, CA (US); Ospedale San Raffaele S.R.L., Milan (IT)

( * ) Notice: Subject to any disclaimer, the term of this patent is extended or adjusted under 35 U.S.C. 154(b) by 1183 days.

(21) Appl. No.: 12/288,847

(22) Filed: Oct. 23, 2008

(65) Prior Publication Data

US 2009/0117617 A1    May 7, 2009

Related U.S. Application Data

(60) Provisional application No. 61/000,333, filed on Oct. 25, 2007.

(51) Int. Cl.
*C12N 15/79* (2006.01)
*C12N 15/87* (2006.01)
*C12N 15/86* (2006.01)

(52) U.S. Cl.
CPC ............ *C12N 15/86* (2013.01); *C07K 2319/81* (2013.01); *C12N 2740/15043* (2013.01); *C12N 2740/15045* (2013.01); *C12N 2840/203* (2013.01)
USPC .......................... 435/320.1; 435/463; 435/475

(58) Field of Classification Search
None
See application file for complete search history.

(56) References Cited

U.S. PATENT DOCUMENTS

| | | |
|---|---|---|
| 5,176,996 A | 1/1993 | Hogan et al. |
| 5,422,251 A | 6/1995 | Fresco |
| 5,789,538 A | 8/1998 | Rebar et al. |
| 5,925,523 A | 7/1999 | Dove et al. |
| 5,994,136 A | 11/1999 | Naldini et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas et al. |
| 6,165,782 A | 12/2000 | Naldini et al. |
| 6,200,759 B1 | 3/2001 | Dove et al. |
| 6,207,146 B1 * | 3/2001 | Tan et al. ............... 424/85.6 |
| 6,242,568 B1 | 6/2001 | Barbas et al. |
| 6,410,248 B1 | 6/2002 | Greisman et al. |
| 6,428,953 B1 | 8/2002 | Naldini et al. |
| 6,453,242 B1 | 9/2002 | Eisenberg et al. |
| 6,534,261 B1 | 3/2003 | Cox et al. |
| 2003/0232410 A1 | 12/2003 | Liljedahl et al. |
| 2005/0026157 A1 | 2/2005 | Baltimore |
| 2005/0064474 A1 | 3/2005 | Urnov et al. |
| 2005/0208489 A1 | 9/2005 | Carroll |
| 2005/0266565 A1 | 12/2005 | Yee et al. |
| 2006/0063231 A1 | 3/2006 | Li et al. |
| 2006/0188987 A1 | 8/2006 | Guschin et al. |
| 2007/0134796 A1 | 6/2007 | Holmes et al. |
| 2007/0218528 A1 | 9/2007 | Miller |
| 2008/0131962 A1 | 6/2008 | Miller |
| 2008/0159996 A1 | 7/2008 | Ando et al. |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2006/010834 A1 | 2/2006 |
| WO | WO 2007/014275 A2 | 1/2007 |
| WO | WO 2007/139982 A2 | 12/2007 |
| WO | WO 2008/005282 | 1/2008 |
| WO | WO 2008/133938 | 11/2008 |

OTHER PUBLICATIONS

Beerli, et al., "Engineering Polydactyl Zinc-Finger Transcription Factors," *Nature Biotechnology* 20:135-141 (2002).
Choo, et al., "Advances in Zinc Finger Engineering," *Curr. Opin. Struct. Biol.* 10:411-416 (2000).
Conese, et al., "Gene Therapy Progress and Prospects: Episomally Maintained Self-Replicating Systems," *Gene Ther.* 11:1735-1741 (2004).
Coquelle, et al., "Expression of Fragile Sites Triggers Intrachromosomal Mammalian Gene Amplification and Sets Boundaries to Early Amplicons," *Cell* 89:215-225 (1997).
Follenzi, et al., "Generation of HIV-1 Derived Lentiviral Vectors," *Methods Enzymol.* 346:454-465 (2002).
Grimes, et al., "Alpha-Satellite DNA and Vector Composition Influence Rates of Human Artificial Chromosome Formation," *Mol. Ther.*, 5:798-805 (2002).
Isalan et al., "A Rapid, Generally Applicable Method to Engineer Zinc Fingers Illustrated by Targeting the HIV-1 Promoter," *Nat Biotechnol* 19:656-660 (2001).
Leavitt, et al., "Human Immunodeficiency Virus Type 1 Integrase Mutants Retain In Vitro Integrase Activity Yet Fail to Integrate Viral DNA Efficiently During Infection," *J. Virol.* 70(2):721-728 (1996).

(Continued)

*Primary Examiner* — Nancy T Vogel
(74) *Attorney, Agent, or Firm* — Pasternak Patent Law; Dahna S. Pasternak

(57) ABSTRACT

Disclosed herein are methods and compositions for targeted integration of one or more copies of a sequence of interest using zinc finger nucleases (ZFNs) comprising a zinc finger protein and a cleavage domain or cleavage half-domain and integrase defective lentiviral donor constructs.

16 Claims, 12 Drawing Sheets

(56) References Cited

OTHER PUBLICATIONS

Nakano, "Epigenetic Assembly of Centromeric Chromatin At Ectopic Alpha-Satellite Sites on Human Chromosomes," *J. Cell Sci.*, 116:4021-4034 (2003).

Ohzeki, et al., "CENP-B Box Is Required for De Novo Centromere Chromatin Assembly on Human Alphoid DNA," *J. Cell Biol.* 159:765-775 (2002).

Pabo, et al., "Design and Selection of Novel CYS2-HIS2 Zinc Finger Proteins," *Ann. Rev. Biochem.* 70:313-340 (2001).

Pauletti, et al., "Early Appearance and Long-Term Persistence of the Submicroscopic Extrachromosomal Elements (Amplisomes) Containing the Amplified DHFR Genes in Human Cell Lines," *Proc. Nat'l Acad. Sci. USA* 87:2955-2959 (1990).

Philippe, et al., "Lentiviral Vectors With a Defective Integrase Allow Efficient and Sustained Transgene Expression in Vitro and in Vivo," *Proc. Nat'l. Acad. Sci. USA* 103(47):17684-17689 (2006).

Rudd, et al., "Human Artificial Chromosomes With Alpha Satellite-Based De Novo Centromeres Show Increased Frequency of Nondisjunction and Anaphase Lag," *Moll. Cell Bio.*, 23:7689-7697 (2003).

Schimke, "Gene Amplification in Cultured Animal Cells," *Cell* 37:705-713 (1984).

Segal, et al., "Custom DNA-Binding Proteins Come of Age: Polydactyl Zinc-Finger Proteins," *Curr. Opin. Biotechnol.* 12:632-637 (2001).

Shinohara, et al., "Stability of Transferred Human Chromosome Fragments in Cultured Cells and in Mice," *Chromosome Res.*, 8:713-725 (2000).

Singer, et al., "Amplification of the Human Dihydrofolate Reductase Gene Via Double Minutes Is Initiated by Chromosome Breaks," *Proc. Nat'l. Acad. Sci. USA* 97:7921-7926 (2000).

Smith, et al., "Multiple Mechanisms of N-Phosphonacetyl-L-Aspartate Resistance in Human Cell Lines: Carbamyl-P Synthetase/Aspartate Transcarbamylase/Dihydro-Orotase Gene Amplification Is Frequent Only When Chromosome 2 Is Rearranged," *Proc. Nat'l. Acad. Sci. USA* 94:1816-1821 (1997).

Suzuki, et al., "Human Artificial Chromosomes Constructed Using the Bottom-Up Strategy Are Stably Maintained in Mitosis and Efficiently Transmissible to Progeny Mice," *J. Biol. Chem.* 281:22615-22623 (2006).

Tlsty, et al., "Differences in the Rates of Gene Amplification in Nontumorigenic and Tumorigenic Cell Lines As Measured by Luria-Delbrück Fluctuation Analysis," *Proc. Nat'l. Acad. Sci. USA* 86:9441-9445 (1989).

Tlsty, et al., "Normal Diploid Human and Rodent Cells Lack a Detectable Frequency of Gene Amplification," *Proc. Nat'l. Acad. Sci. USA* 87:3132-3139 (1990).

Wright, et al., "DNA Amplification Is Rare in Normal Human Cells," *Proc. Nat'l. Acad. Sci. USA* 87:1791-1795 (1990).

Apolonia, et al., "Stable Gene Transfer to Muscle Using Non-Integrating Lentiviral Vectors," *Molecular Therapy* 15:194-1954 (2007).

Cornu, et al., "Targeted Genome Modifications Using Integrase-Deficient Lentiviral Vectors," *Molecular Therapy* 15:2107-2113 (2007).

Lombardo, et al., "Gene Editing in Human Stem Cells Using Zinc Finger Nucleases and Integrase-Defective Lentiviral Vector Delivery," *Nature Biotechnology* 25:1298-1306 (2007).

Moehle, et al., "Targeted Gene Addiction Into a Specified Location in the Human Genome Using Designed Zinc Finger Nucleases," *PNAS* 104:3055-3060 (2007).

\* cited by examiner

Figure 1
A. Lentiviral construct I
B. Lentiviral construct II
C. Lentiviral construct III
D. Lentiviral construct IV
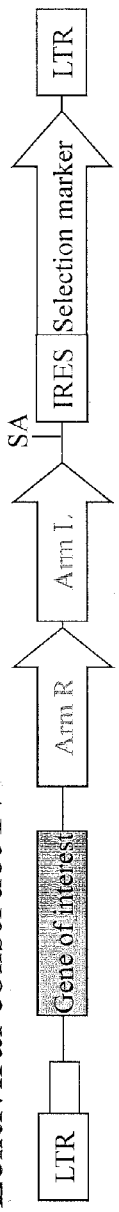
E. Lentiviral construct V
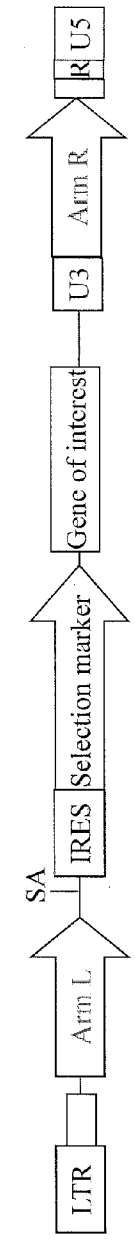

Figure 2 Lentiviral construct I
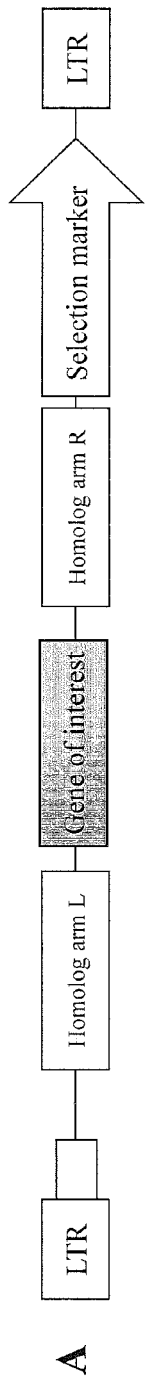
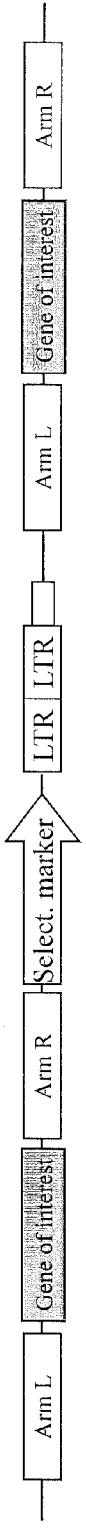
A.
B. Negative selection
Non-modified cells, HR-EJ and single copy HR-TI
C. Positive selection
Random integration, LTR-EJ, HR-EJ and multiple copy HR-TI:

Figure 3  Lentiviral construct II

A). Marker 1 positive selection: all the cells with single copy HR-TI, or with some HR-EJ (very low efficiency).

B). Marker 2 positive selection: all the cells with multiple copy HR-TI, plus all the cells with random integration, LTR-EJ and some HR-EJ (very low efficiency).

C). Marker 1 positive selection plus marker 2 negative selection: mainly cells with Single copy HR-TI only, but without multiple copy HR-TI, random integration, LTR-EJ.

D). Marker 2 positive selection plus marker 1 negative selection: all the cells with multiple copy HR-TI only, plus all the cells with random integration, LTR-EJ and some HR-EJ (very low efficiency), but without single copy HR-TI.

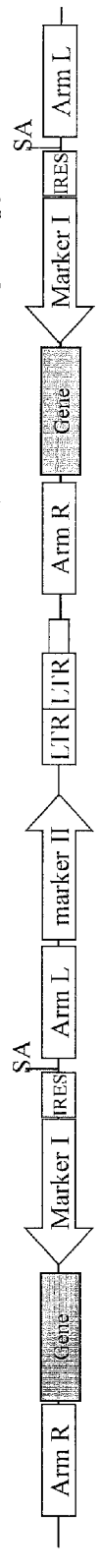

E). Marker 1 positive selection plus marker 2 positive selection: mainly cells with both multiple copy HR-TI and single copy HR-TI.

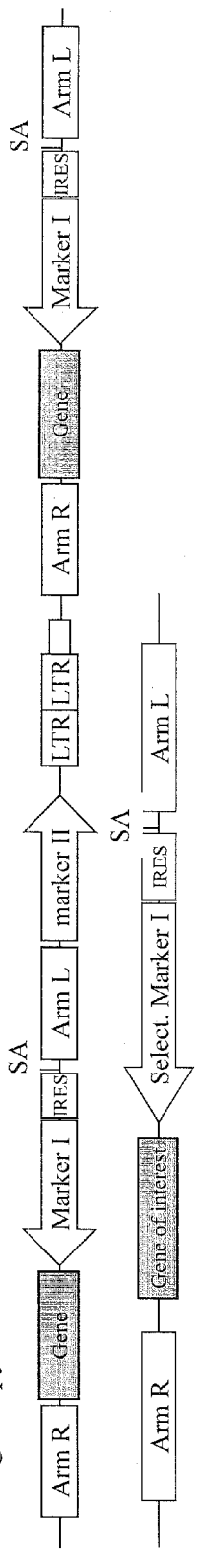

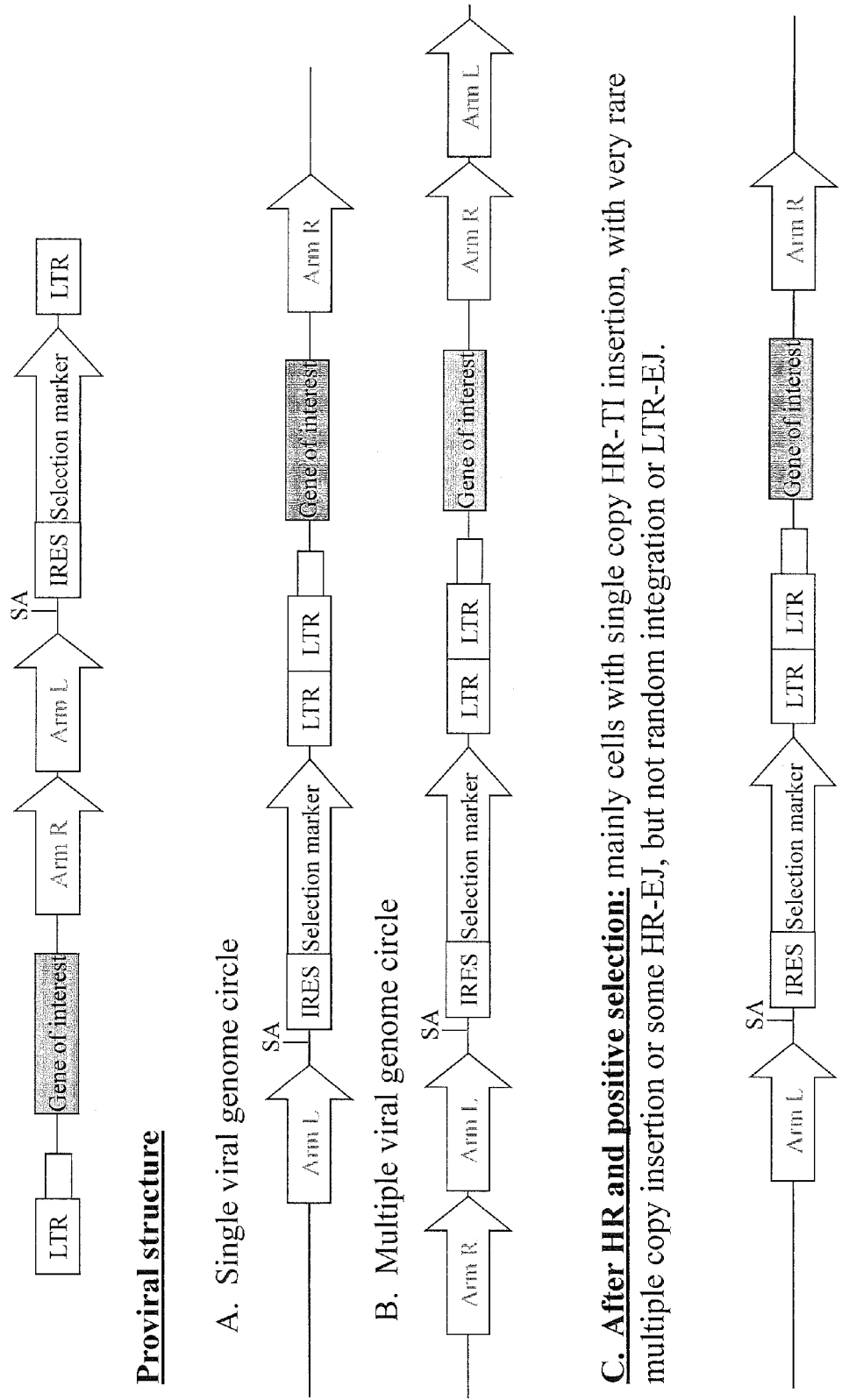

Figure 5     Lentiviral construct V

Proviral structure

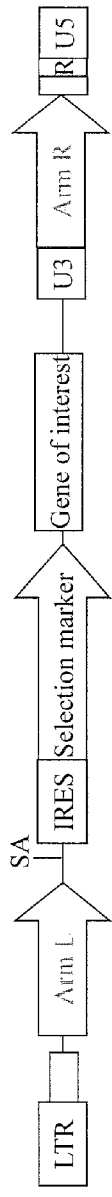

A. Single viral genome circle

B. Multiple viral genome circle

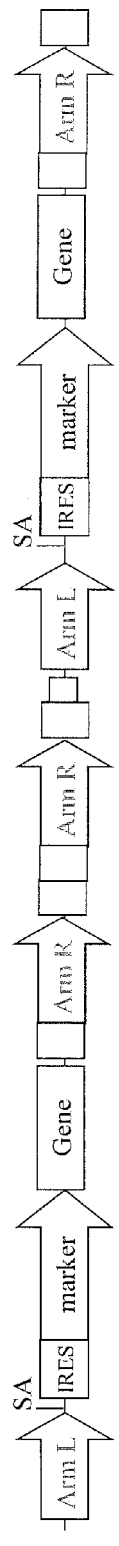

C. After HR and positive selection: mainly cells with single copy HR-TI insertion, with very rear multiple copy insertion, without random integration or LTR-EJ. This construct leaves the smallest Lentiviral sequence in the target genome to achieve high safety.

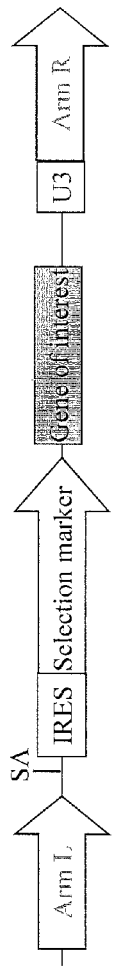

Identification of different type TIs in K562 single cell clones by PCRs

| | | Ad5/35 224nf | Ad5/35 224 | Ad5/35 215 |
|---|---|---|---|---|
| Target Intergrations | HR Heterozygous | 4/12 (33.3%) | 19/48 (39.6%) | 19/45 (42.2%) |
| | HR homozygous | 0/12 | 1/48 (2.1%) | 1/45 (2.2%) |
| | LTR_EJ | 0/12 | 0/48 | 1/45 (2.2%) |
| | Multiple copy HR | 4/12 (33.3%) | 15/48 (31.3%) | 15/45 (33.3%) |
| | Hetero, LTR_EJ | 0/12 | 1/48 (2.1%) | 0/45 |
| | Hetero, Multiple | 4/12 (33.3%) | 6/48 (12.5%) | 5/45 (11.1%) |
| | Homo with multiple | 0/12 | 1/48 (2.1%) | 2/45 (4.4%) |
| | Multiple, EJ | 0/12 | 3/48 (6.3%) | 2/45 (4.4%) |
| Random integration | | 0/12 | 2/48 (4.2%) | 0/45 |

* NIL_R5_pgk-eGFP donor at moi=7.5

Molecular conformation of pgk-eGFP TI in k562 cells

Molecular conformation of pgk-eGFP TI in Hep3B and hMSC

Pgk-eGFP probe

Ad5/35-ZFN plus NIL induce pgk-eGFP TI at CCR5 locus in hMSCs hMSC with target integration at CCR5 locus *in vitro* osteogenesis differentiation

METHODS AND COMPOSITIONS FOR TARGETED INTEGRATION

CROSS-REFERENCE TO RELATED APPLICATIONS

The present application claims the benefit of U.S. Provisional Application No. 61/000,333, filed Oct. 25, 2007; the disclosure of which is hereby incorporated by reference in its entirety herein.

STATEMENT OF RIGHTS TO INVENTIONS MADE UNDER FEDERALLY SPONSORED RESEARCH

Not applicable.

TECHNICAL FIELD

The present disclosure is in the fields of polypeptide and genome engineering and homologous recombination.

BACKGROUND

Stable transgenesis and targeted gene insertion have many potential applications in both gene therapy and cell engineering. However, current strategies are often inefficient and non-specifically insert the transgene into prokaryotic or eukaryotic genomic DNA. The inability to control the location of genome insertion can lead to highly variable levels of transgene expression throughout the population due to position effects within the genome. Additionally, current methods of stable transgenesis and amplification of transgenes often result in physical loss of the transgene, transgene silencing overtime, insertional mutagenesis by the integration of a gene and autonomous promoter inside or adjacent to an endogenous gene, the creation of chromosomal abnormalities and expression of rearranged gene products (comprised of endogenous genes, the inserted transgene, or both), and/or the creation of vector-related toxicities or immunogenicity in vivo from vector-derived genes that are expressed permanently due to the need for long-term persistence of the vector to provide stable transgene expression.

Lentiviral and retroviral vectors have been used for gene integration and can stably integrate their viral genomes along with an encoded transgene into the host genome of transduced cells via integrase. See, e.g., U.S. Pat. Nos. 5,994,136; 6,165,782; and 6,428,953. However, transgene expression can be highly variegated depending on where the virus integrates in the host genome, transgene silencing can occur over time, insertional mutagenesis can occur, and the site of integration can not be controlled. Furthermore, the number of transgene copies inserted into the genome can only be somewhat controlled by the dose of the vector added to the cells. Also, if the viral vector expresses additional, non-native genes, these can be toxic to the cells or can cause an immune response that leads to the destruction of the transduced cell in vivo.

In eukaryotic cells, stable transgenesis can also be achieved using a recombinant DNA sequence encoding a selection marker along with the transgene of interest. Cells that stably express the transgene of interest can be isolated by selecting for stable expression of the selection marker. The number of transgene copies and the level of expression can be amplified by prolonged selection using drugs such as methotrexate (DHFR gene) or PALA (CAD gene). However, this approach still suffers from position effects and can not allow for the targeting of where genes can be inserted into the genome. (Coquelle et al. (1997) Cell 89:215-225). In addition, the amplification frequency is low (typically <10E-4) and often requires selection to occur for 20 cell generations with gradually increasing drug concentration and amplification using a single selection step is extremely inefficient (Tlisty et al. (1989) Proc. Nat'l. Acad. Sci. USA 86: 9441-9445; Kempe et al. (1976) Cell 9:541-550; Singer et al. (2000) Proc. Nat'l. Acad. Sci. USA 97:7921-7926). Furthermore, amplification can only be carried out in tumor cells and does not work in primary cells (Tlisty (1990) Proc. Nat'l. Acad. Sci. USA 87:3132-3139; Wright et al. (1990) Proc. Nat'l. Acad. Sci. USA 87:1791-1795) and, in many human and rat cell lines, the amplification protocol can lead to the formation of unstable extrachromosomal double minutes instead of homogenous repeats of the chromosomal region encoding the selection marker and transgene of interest and/or to a greater occurrence of chromosomal instability and rearrangements in tumor cells (Pauletti et al. (1990) Proc. Nat'l. Acad. Sci. USA 87:2955-2959; Smith et al. (1997) Proc. Nat'l. Acad. Sci. USA 94:1816-1821; Fougere-Deschatrette et al. (1982) in Gene Amplification, ed. Schimke, R. T. (Cold Spring Harbor Lab. Press, Plainview, N.Y., pp. 29-32; Singer et al. (2000) Proc. Nat'l. Acad. Sci. USA 97:7921-7926). Stable, high transgene expression also often requires continued exposure to the selection drug (Schimke, R. T. (1984) Cell 37:705-713; Stark et al (1984), Annual Rev. Biochem., 53:447-503; Tlisty et al. (1989) Proc. Nat'l. Acad. Sci. USA 86:9441-9445). Thus, given the requirement for prolonged exposure to drugs, increase in chromosomal instability, and inability to use this method for primary cells, marker selection is not applicable in the engineering of cells for cellular therapies.

Single or multiple copies of a transgene can also be stably integrated into cells via artificial chromosomes or stable episomes. These systems can replicate and remain stable in mammalian cells, contain large gene payloads that can include genomic regulatory elements and generally do not integrate to cause insertional mutagenesis (Conese et al (2004) vol. 11, pp. 1735-1741). However, there have been issues with their overall stability over time including, for example, loss and/or rearrangement of these artificial chromosomes as well as an increase in the integration of the artificial chromosomes or episomes into the native chromosomes over time, which can cause de-stabilization of the native chromosome(s) (e.g. creation of a dicentric chromosome (Suzuki N. et al (2006), JBC, vol. 281, pp. 26615-26623; Shinohara T. et al (2000) Chromosome Res., vol. 8, pp. 713-725; Ohzeki J., et al (2002) J. Cell Biol, vol. 159, pp. 765-775; Grimes B R, et al. (2002) Mol Ther, Vol. 5, pp. 798-805; Nakano M, (2003) J Cell Sci, vol. 116, pp. 4021-4034). Furthermore, artificial chromosomes and stable episomes function only in dividing cell lines or proliferating primary cells where DNA-based delivery (e.g. electroporation or cationic lipids) works efficiently (Suzuki N. et al (2006), JBC, vol. 281, pp. 26615-26623) and segregation errors occur that cause instability and loss over time (Rudd M K, et al (2003) Mol Cell Bio, Vol. 23, pp. 7689-7697). In addition, the isolation and maintenance of cell clones containing these stable episomes or artificial chromosomes require selection-based methods and, accordingly, have all the problems detailed above. Finally, safety concerns are raised by the fact that these stable episomes are often derived from self-replicating viral-based vectors (e.g. EBV or bovine papilloma virus) that have been shown to persist extrachromosomally in mammalian cells, but require the expression of an oncogenic viral-derived transgene such as EBNA1.

Zinc finger nucleases can be used to efficiently drive targeted gene insertion at extremely high efficiencies using a homologous donor template to insert novel gene sequences into the break site via homology-driven repair (HDR). See, for example, United States Patent Publications 20030232410; 20050208489; 20050026157; 20050064474; and 20060188987, and International Publication WO 2007/014275, the disclosures of which are incorporated by reference in their entireties for all purposes. This does not require long-term persistence of the delivery vector, avoiding issues of insertional mutagenesis and toxicities or immunogenicity from vector-derived genes.

However, there remains a need for controlled, site-specific integration of a single or multiple copies of a transgene to allow for higher or lower, but stable and uniform, transgene expression within a cell population. There also remains a need for targeted gene integration that does not result in variegated transgene expression, insertional mutagenesis caused by position effects or chromosomal instability related to transgene amplification.

SUMMARY

Disclosed herein are compositions and methods for controlled site-specific integration into the genome. The compositions and methods described herein allow for the controlled integration of a single or multiple copies of a selected transgene. Thus, depending on the application and the desired level of transgene expression, the present disclosure allows for a single copy or multiple copies of a transgene to be inserted into a specific site in a target genome.

In particular, the present disclosure provides methods and compositions for expressing an exogenous polynucleotide (e.g. transgene) carried by an integrase-defective lentivirus vector (IDLV) in a cell. The transgene can comprise, for example, one or more genes or cDNA molecules, or any type of coding or noncoding sequence, and is introduced into the cell such that it is integrated into the genome of the cell in a predetermined region of interest. Integration of the transgene is facilitated by targeted double-strand cleavage of the genome in the region of interest. Cleavage is targeted to a particular site through the use of fusion proteins comprising a zinc finger binding domain, which can be engineered to bind any sequence of choice in the region of interest, and a cleavage domain or a cleavage half-domain. Such cleavage stimulates targeted integration of exogenous polynucleotide sequences at or near the cleavage site.

Cells that can be used with these compositions and methods include cultured cells, cells in an organism and cells that have been removed from an organism for treatment in cases where the cells and/or their descendants will be returned to the organism after treatment. A region of interest in cellular chromatin can be, for example, a genomic sequence or portion thereof. Cellular chromatin can be present in any type of cell including, but not limited to, prokaryotic and eukaryotic cells, fungal cells, plant cells, animal cells, mammalian cells, primate cells and human cells.

In one aspect, disclosed herein are integrase defective lentiviral (IDLV) donor polynucleotides. The donor polynucleotides can further comprise an exogenous nucleic acid sequences. The donor polynucleotides are typically flanked by the LTRs of the IDLV. Further, the donor polynucleotides of the IDLVs comprise first and second polynucleotides (homology arms) that are homologous to sequences of interest in the cell. The homology arms may flank the sequence encoding the transgene or, alternatively, the exogenous sequence may be outside the homology arms. One or both of the homology arms may be identical to sequences in the region of interest. Alternatively, one or both of the homology arms may be homologous but non-identical to sequences in the region of interest.

Any of the IDLV donor polynucleotides described herein may further comprise one or more selectable markers, for example one or more positive and/or negative selection markers. In certain embodiments, a single positive and/or negative selection marker is outside of the homology arms. In other embodiments, the IDLV donor polynucleotide comprises two selectable markers, one flanked by the homology arms and one outside the homology arms. Any selectable marker or combination of selectable markers can be used, for example a single positive selection marker, a single negative selection marker, two positive selection markers, two negative selection markers, and one negative with one positive selection marker. Any of the selection markers may also be positive/negative selection markers, for example hyg-TK selection markers. In certain embodiments, the IDLV donor polynucleotide comprises a vector as shown in FIG. 1A, FIG. 1B, FIG. 1C, FIG. 1D or FIG. 1E.

Any of the IDLV donor polynucleotides may alternatively comprise one or more screening markers, for example, Green Fluorescent Protein (GFP) or beta-galactosidase. In certain embodiments, the screening marker is outside the homology arms while in other embodiments, the screening marker is inside the homology arms. In additional embodiments, one screening marker is used in combination with one selection marker, where one is flanked by the homology arms and the other is outside the homology arms. Any combination of screening and selectable markers can be used, for example, a screening marker may be used that is located between the homology arms in combination with a selection marker that is outside the homology arms. Additionally, any combination of markers can be used, for example one screening marker used with one positive selection marker, and one screening marker used with one negative screening marker.

In another aspect, disclosed herein is a method for controlled integration of one or more copies of an exogenous nucleic acid sequence into a cell, the method comprising: (a) expressing a first fusion protein in the cell, the first fusion protein comprising a first zinc finger binding domain and a first cleavage half-domain, wherein the first zinc finger binding domain has been engineered to bind to a first target site in a region of interest in the genome of the cell; (b) expressing a second fusion protein in the cell, the second fusion protein comprising a second zinc finger binding domain and a second cleavage half domain, wherein the second zinc finger binding domain binds to a second target site in the region of interest in the genome of the cell, wherein the second target site is different from the first target site; and (c) contacting the cell with any of the IDLV donor polynucleotides as described herein; wherein binding of the first fusion protein to the first target site, and binding of the second fusion protein to the second target site, positions the cleavage half-domains such that the genome of the cell is cleaved in the region of interest, thereby resulting in integration of one or more copies of the exogenous sequence into the genome of the cell in the region of interest and expression of the product of the exogenous sequence. In certain embodiments, the fusion proteins comprising the first and second zinc finger proteins are provided on an adenovirus (Ad) vector, for example an Ad5/35 vector.

Any of the methods described herein may be used to select for cells containing a single copy of the exogenous sequence (transgene) that has been inserted into the region for interest. In certain embodiments, a single copy of the transgene is integrated using an IDLV donor polynucleotide comprising a negative marker outside the homology arms (FIG. 2B). In other embodiments, a single copy of the transgene is integrated using an IDLV donor polynucleotide comprising a positive selection marker flanked by the homology arms (FIG. 3A). In other embodiments, a single copy of the transgene is integrated using an IDLV donor polynucleotide comprising a positive selection marker flanked by the homology arms and a negative selection marker outside the homology arms (FIG. 3C). In still other embodiments, a single copy of the transgene is integrated using an IDLV donor polynucleotide where both the transgene and selection marker (e.g., positive selection marker) are outside the homology arms (FIG. 4C). In yet other embodiments, a single copy of transgene is integrated using an IDLV donor polynucleotide as shown in FIG. 1E and FIG. 5.

In addition, any of the methods described herein may be used to select for insertion of multiple copies of the exogenous sequence into the region of interest. "Multiple copies" refers to cells which have 2, 3, 4 or more copies of the transgene integrated into one or more alleles of the target. In certain embodiments, multiple copies of the transgene are integrated using an IDLV donor polynucleotide comprising a positive marker outside the homology arms (FIGS. 2C and 3B). In other embodiments, multiple copies of the transgene are integrated using an IDLV donor polynucleotide comprising a positive selection marker outside the homology arms and a negative selection marker flanked by the homology arms (FIG. 3D). In yet other embodiments, a single copy and multiple copies of the transgene are integrated using an IDLV donor polynucleotide comprising a positive selection marker flanked by the homology arms and a positive selection marker outside the homology arms (FIG. 3E).

In any of the methods described herein, the region of interest may be in a region of the genome that is not essential for viability. For example, the PPP1R12C locus in human cells may be used as a 'safe harbor' locus for targeted integration (see U.S. Patent Publication No. 20080299580). In other embodiments, the region of interest is in a region of the genome that is transcriptionally active. In embodiments in which the region of interest is in a region of the genome that is essential for viability, the insertion does not substantially alter expression of the "essential" gene.

In any of the methods described herein, the first and second cleavage half-domains are from a Type IIS restriction endonuclease, for example, FokI or StsI. Furthermore, in any of the methods described herein, at least one of the fusion proteins may comprise an alteration in the amino acid sequence of the dimerization interface of the cleavage half-domain.

In any of the methods described herein, the cell can be a mammalian cell, for example, a human cell. Furthermore, the cell may be arrested in the G2 phase of the cell cycle.

The present subject matter thus includes, but is not limited to, the following embodiments:

1. An integrase-defective lentiviral (IDLV) donor polynucleotide comprising, between the lentivirus LTRs,
   (i) first and second nucleotide sequences that are homologous sequences to a region of interest of cellular chromatin of a cell; and
   (ii) an exogenous sequence.

2. The IDLV donor polynucleotide of 1, further comprising a sequence encoding a first selectable or screening marker.

3. The IDLV donor polynucleotide of 2, wherein the first selectable or screening marker is not between the first and second nucleotide sequences.

4. The IDLV donor polynucleotide of any of 2 to 3, further comprising a sequence encoding a second selectable or screening marker.

5. The IDLV donor polynucleotide of 4, wherein the second selectable or screening marker is flanked by the first and second nucleotide sequences.

6. The IDLV donor polynucleotide of any of 2 to 5, wherein the first and/or second selectable marker is a positive selection marker.

7. The IDLV donor polynucleotide of any of 2 to 5, wherein the first and/or second selectable marker is a negative selection marker.

8. The IDLV donor polynucleotide of any of 2 to 5, wherein the first and/or second selectable marker is a positive and a negative selection marker.

9. The IDLV donor polynucleotide of 8, wherein the positive-negative selection marker is hyg-TK.

10. The IDLV donor polynucleotide of any of 1 to 9, wherein the cell is eukaryotic cell.

11. The IDLV donor polynucleotide of 10, wherein the cell is a mammalian cell.

12. The IDLV donor polynucleotide of 11, wherein the cell is a human cell.

13. The IDLV donor polynucleotide of any of 1 to 12, wherein the first and second nucleotides flank the exogenous sequence.

14. A method for controlled, site-specific integration of a single copy or multiple copies of an exogenous nucleic acid sequence into a cell, the method comprising:
   (a) expressing a first fusion protein in the cell, the first fusion protein comprising a first zinc finger binding domain and a first cleavage half-domain, wherein the first zinc finger binding domain has been engineered to bind to a first target site in a region of interest in the genome of the cell;
   (b) expressing a second fusion protein in the cell, the second fusion protein comprising a second zinc finger binding domain and a second cleavage half domain, wherein the second zinc finger binding domain binds to a second target site in the region of interest in the genome of the cell, wherein the second target site is different from the first target site; and
   (c) contacting the cell with any of the IDLV donor polynucleotides of any of 1 to 13;
   wherein binding of the first fusion protein to the first target site, and binding of the second fusion protein to the second target site, positions the cleavage half-domains such that the genome of the cell is cleaved in the region of interest, thereby resulting in integration of one or more copies of the exogenous sequence into the genome of the cell in the region of interest.

15. The method according to 14, wherein the exogenous nucleic acid sequence comprises a cDNA.

16. The method according to 14 or 15, wherein the region of interest is in an accessible region of cellular chromatin.

17. The method of 14, 15 or 16, wherein the region of interest is in a region of the genome that is not essential for viability.

18. The method of any of 14 to 17, wherein the region of interest is in a region of the genome that is transcriptionally active.

19. The method of any of 14 to 18, wherein a single copy of the exogenous sequence is integrated into the genome of the cell.

20. The method of any of 14 to 18, wherein multiple copies of the exogenous sequence are integrated into the genome of the cell.

21. The method according to any of 14 to 20, wherein the first and second cleavage half-domains are from a Type IIS restriction endonuclease.

22. The method according to 21, wherein the Type IIS restriction endonuclease is selected from the group consisting of FokI and StsI.

23. The method according to any of 14 to 22, wherein the region of interest is in a chromosome.

24. The method according to any of 14 to 23, wherein the region of interest comprises a gene.

25. The method according to any of 14 to 24, wherein the cell is arrested in the G2 phase of the cell cycle.

26. The method according to any of 14 to 25, wherein at least one of the fusion proteins comprises an alteration in the amino acid sequence of the dimerization interface of the cleavage half-domain.

27. The method according to any of 14 to 26, wherein the cell is a mammalian cell.

28. The method according to 27, wherein the cell is a human cell.

BRIEF DESCRIPTION OF THE DRAWINGS

FIG. 1, panels A to C, are schematics depicting exemplary integrase defective lentivirus (IDLV) donor constructs for controlled and targeted integration. FIG. 1A is a schematic of a lentiviral construct that includes one selection or screening marker and designated "lentiviral construct I." FIG. 1B is a schematic of a lentiviral construct that comprises two selection or screening markers and is designated "lentiviral construct II." FIG. 1C is a schematic of a lentiviral donor construct without a selectable or screening marker. FIG. 1D is a schematic of a lentiviral donor construct that includes one selectable or screening marker outside the homology arms and is designated "lentiviral construct IV." FIG. 1E is a schematic of a lentiviral donor construct designated "lentiviral construct V."

FIG. 2, panels A to C, depict various exemplary embodiments of lentiviral construct I. FIG. 2A shows the construct generally. FIG. 2B depicts a construct in which the selection or screening marker is a negative selection marker. As indicated, negative selection can result in non-modified cells, or cells in which a single copy is integrated into the genome via homologous recombination targeted integration (HR-TI) and/or by homologous recombination at one end and end-joining of the other end (HR-EJ). FIG. 2C depicts a construct in which the selection or screening marker is a positive selection marker and which introduces multiple copies of the gene of interest, typically in a head-to-tail orientation. The construct shown in FIG. 2C can also result in random integration, integration of the LTRs by end-joining (LTR-EJ) or integration of a single copy of the gene of interest via homologous recombination at one end and end-joining of the other end (HR-EJ).

FIG. 3 depicts various exemplary embodiments of lentiviral construct II. The top line shows the construct generally. FIG. 3A indicates that a single copy of the gene of interest is integrated into the target cells when selection/screening marker 1 is a positive selection marker. This construct also results in low levels of cells containing a single copy of the gene of interest due to homologous recombination at one end and end-joining of the other end (HR-EJ). FIG. 3B depicts a construct in which selection/screening marker 1 is a positive selection marker and which introduces multiple copies of the gene of interest, typically in a head-to-tail orientation. The construct described in FIG. 3B can also result in random integration, integration of the LTRs by end-joining (LTR-EJ) or integration of a single copy of the gene of interest via homologous recombination at one end and end-joining of the other end (HR-EJ). FIG. 3C shows targeted integration via homologous recombination (HR-TI) of a single copy of the gene of interest when selection/screening marker 1 is a positive selection marker and selection/screening marker 2 is a negative selection marker. The construct of FIG. 3C can also be randomly integrated or integrated via LTR end-joining (LTR-EJ). FIG. 3D shows that multiple copies of the gene of interest are integrated into the target cells by homologous recombination when selection/screening marker 1 is a negative selection marker and selection/screening marker 2 is a positive selection marker. The construct can also result in random integration, LTR-EJ and HR-EJ (at low efficiencies), but does not allow integration of a single copy via HR-TI. FIG. 3E shows how both single and multiple copies of the gene of interest are integrated into the target cells when selection/screening marker 1 is a positive selection marker and selection/screening marker 2 is a positive selection marker.

FIG. 4 depicts various exemplary embodiments of lentiviral construct IV as shown in FIG. 1D. The top line shows the construct generally. Notably, the exogenous sequence (transgene) is outside of the homology arms. FIGS. 4A and 4B show the proviral structure of a single (FIG. 4A) and multiple (FIG. 4B) genome circle(s). As shown, the homologous arms flank the transgene after the 2-LTR circle forms in cells. FIG. 4C shows how after homologous recombination of a construct including a positive selection marker, positive selection gives rise to cells that contain a single copy of the transgene via HR-TI. Rarely, cells with multiple copies or HR-EJ will be selected for, but positive selection for this construct kills cells with randomly integrated or LTR-EJ integrated transgenes.

FIG. 5 depicts various exemplary embodiments of lentiviral construct V as shown in FIG. 1E. The top line shows the construct generally. FIGS. 5A and 5B show the proviral structure of a single (FIG. 5A) and multiple (FIG. 5B) genome circle(s). FIG. 5C shows how, after homologous recombination of a construct including a positive selection marker, positive selection gives rise to cells that contain a single copy of the transgene via HR-TI. Rarely, cells with multiple copies or HR-EJ will be selected for, but positive selection for this construct kills cells with randomly integrated or LTR-EJ integrated transgenes.

FIG. 7A depicts results when the blots were probed with a PGK-GFP probe. FIG. 7B shows results using a probe directed to the left homology arm of the construct (CCR5 left arm probe).

FIGS. 10A and B show GFP expression in cells comprising the ZFNs and donor constructs. FIGS. 10C and D show lack of expression in cells comprising only the donor constructs. FIG. 10E is a graph depicting GFP expression over 8 passages at the indicated multiplicity of infection (moi) of the donor construct.

FIGS. 11A, 11B and 11C show GFP expression. FIGS. 11D and 11E show unstained GFP-expressing cells that have differentiated into adipocytes and FIG. 11F shows Oil Red O staining of GFP-expressing cells that have differentiated into adipocytes.

FIGS. 12A and 12B show GFP expression. FIG. 12C shows unstained GFP-expressing cells and FIG. 12D shows ALP staining of GFP-expressing osteogenic differentiated cells.

DETAILED DESCRIPTION

Figure 6:
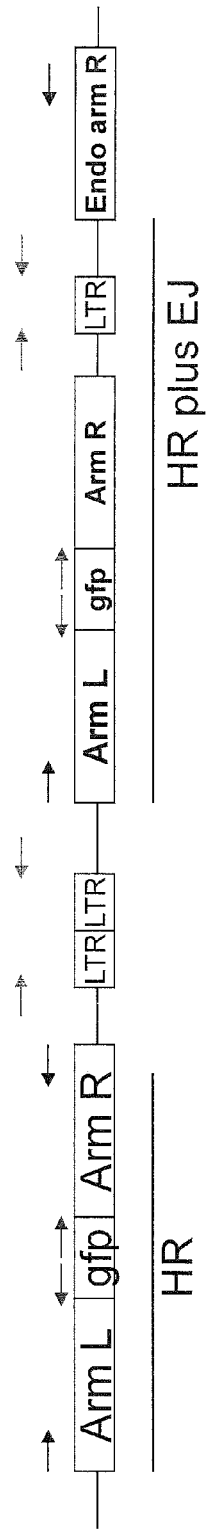
FIG. 6 shows integration of an IDLV lentiviral donor construct into K562 cells in the presence of ZFNs targeted to CCR5. The IDLV donor construct included in a 5' to 3' direction LTR-left homology arm-GFP-encoding sequence-right homology arm-LTR. The left and right homology arms were homologous to CCR5. The ZFNs shown were all delivered using an Ad5/35 vector. See, U.S. Pat. No. 7,951,925. "224nf" refers to ZFN 224 without a FLAG tag. "224" refers to ZFN 224 with a FLAG tag. ZFN 224 comprises engineered cleavage domains of FokI. "215" refers to ZFN 215, which comprises wild-type FokI cleavage domains. "HR heterozygous" refers to targeted integration of a single copy via homologous recombination on one allele. "HR homozygous" refers to targeted integration of a single copy via homologous recombination on both alleles. "LTR_EJ" refers to cells in which the construct was integrated by end joining of the LTRs. "Multiple copy HR" refers to targeted integration of multiple copies of the GFP construct on one allele. "Hetero LTR_EJ" refers to targeted integration of a single copy via HDR on one allele and LTR-EJ on another allele. "Hetero multiple" refers to targeted integration of a single copy via homologous recombination on one allele and multiple copies via HDR on another allele. "Homo with multiple" refers to targeted integration of multiple copies via homologous recombination on both alleles and "multiple EJ" refers to integration of multiple copies of the donor construct via HDR on one allele and integration via end-joining on another allele.

The present disclosure relates to methods and composition for targeted integration (TI) into a target genome, particularly a mammalian (e.g., human) genome. The compositions and methods allow for site-specific, controlled integration of single or multiple (2, 3, 4, 5, 6 or more) copies of a gene of interest into a target cell.

Compositions useful for targeted cleavage and recombination include fusion proteins comprising a cleavage domain (or a cleavage half-domain) and a zinc finger binding domain, polynucleotides encoding these proteins and combinations of polypeptides and polypeptide-encoding polynucleotides. A zinc finger binding domain can comprise one or more zinc fingers (e.g., 2, 3, 4, 5, 6, 7, 8, 9 or more zinc fingers), and can be engineered to bind to any sequence. The presence of such a fusion protein (or proteins) in a cell will result in binding of the fusion protein(s) to its (their) binding site(s) and cleavage within the endogenous target gene.

Also disclosed herein are replication-defective adenovirus (Ad) vectors comprising ZFNs and/or donor sequences and cells comprising these Ad vectors. These Ad vectors are useful in methods for targeted cleavage of cellular chromatin and for targeted alteration of a cellular nucleotide sequence, e.g., by targeted cleavage followed by non-homologous end joining or by targeted cleavage followed by homologous recombination between an exogenous polynucleotide (comprising one or more regions of homology with the cellular nucleotide sequence) and a genomic sequence.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS N MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

An "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 20050064474 and 20060188987 and U.S. Provisional Application No. 60/808,486 (filed May 25, 2006), incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be a gene derived from another species, for example a human gene sequence integrated into a hamster genome.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eukaryotic" cells include, but are not limited to, fungal cells (such as yeast), plant cells, animal cells, mammalian cells and human cells (e.g., T-cells).

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Zinc Finger Nucleases

The IDLV donor polynucleotides described are preferably integrated in a site-specific manner (targeted integration) using zinc finger nucleases (ZFNs). ZFNs comprise a zinc finger protein (ZFP) and a nuclease (cleavage) domain.

A. Zinc Finger Proteins

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned WO 02/077227.

Selection of target sites; ZFPs and methods for design and construction of fusion proteins (and polynucleotides encoding same) are known to those of skill in the art and described in detail in related to U.S. Publication Nos. 20030232410; 20050208489; 2005064474; 20050026157; 20060188987; 20070218528 and 20070134796; and International Publication WO 07/014,275; the disclosures of which are incorporated by reference in their entireties for all purposes.

In certain embodiments, the ZFNs described herein are carried on an adenovirus vector, for example the chimeric Ad5/35 vector. As noted herein, the ZFNs may comprise 2, 3, 4, 5, 6 or even more zinc finger domains.

A ZFP binding domain is fused to a cleavage domain or cleavage half-domain of a nuclease. In certain embodiments, the ZFP is fused to a cleavage half-domain of a Type IIs restriction endonuclease, for example FokI. When fused to a cleavage half-domain, a pair of such zinc finger/nuclease half-domain fusions are used for targeted cleavage, as disclosed, for example, in U.S. Patent Publication No. 20050064474.

For targeted cleavage, the near edges of the binding sites can separated by 5 or more nucleotide pairs, and each of the fusion proteins can bind to an opposite strand of the DNA target.

B. Cleavage Domains

As noted above, the ZFNs also comprise a nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474, 20060188987 and 2008/0131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499. See FIGS. 2, 3 and 4.

Thus, in one embodiment, as shown in FIGS. 3 and 4, the mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., Example 1 of U.S. Patent Publication No. 20080131962, the disclosure of which is incorporated by reference in its entirety for all purposes.

Engineered cleavage half-domains described herein can be prepared using any suitable method, for example, by site-directed mutagenesis of wild-type cleavage half-domains (Fok I) as described in U.S. Patent Publication Nos. 20050064474 and 20070134796.

C. Additional Methods for Targeted Integration

Any nuclease having a target site in the target gene can be used in the methods disclosed herein. For example, homing endonucleases and meganucleases have very long recognition sequences, some of which are likely to be present, on a statistical basis, once in a human-sized genome. Any such nuclease having a unique target site in a target gene can be used instead of, or in addition to, a zinc finger nuclease, for targeted cleavage in a target gene.

Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dijon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

Although the cleavage specificity of most homing endonucleases is not absolute with respect to their recognition sites, the sites are of sufficient length that a single cleavage event per mammalian-sized genome can be obtained by expressing a homing endonuclease in a cell containing a single copy of its recognition site. It has also been reported that the specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66.

Donor Polynucleotides

The nucleases described herein (e.g., ZFNs) stimulate targeted integration of a sequence by cleaving double-stranded DNA. The sequence integrated into the genome at or near the cleavage site is referred to as the donor polynucleotide or donor sequence. The donor sequence typically contains sufficient homology to a genomic sequence to support homologous recombination between it and the genomic sequence to which it bears homology. Approximately 25, 50 100 or 200 nucleotides or more of sequence homology between a donor and a genomic sequence (or any integral value between 10 and 200 nucleotides, or more) will support homologous recombination therebetween. Donor sequences can range in length from 10 to 5,000 nucleotides (or any integral value of nucleotides therebetween) or longer. It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology is present to support homologous recombination.

Alternatively, a donor sequence can contain a non-homologous sequence flanked by two regions of homology. Additionally, donor sequences can comprise a vector molecule containing sequences that are not homologous to the region of interest in cellular chromatin. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

To simplify assays (e.g., hybridization, PCR, restriction enzyme digestion) for determining successful insertion of the donor sequence, certain sequence differences may be present in the donor sequence as compared to the genomic sequence. Preferably, if located in a coding region, such nucleotide sequence differences will not change the amino acid sequence, or will make silent amino acid changes (i.e., changes which do not affect the structure or function of the protein). The donor polynucleotide can optionally contain changes in sequences corresponding to the zinc finger domain binding sites in the region of interest, to prevent cleavage of donor sequences that have been introduced into cellular chromatin by homologous recombination.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV (e.g. AAV vectors that concatenate), lentivirus). In addition, sequences in a donor polynucleotide may be subject to codon optimization to allow for optimal expression, where the donor nucleotide codons found in one species may be altered at the nucleic acid level to the nucleotide codons preferred in the recipient genome.

In certain embodiments, the donor polynucleotide is a lentiviral donor polynucleotide. Lentiviral transfer vectors can be produced generally by methods well known in the art. See, e.g., U.S. Pat. Nos. 5,994,136; 6,165,782; and 6,428,953. Preferably, the lentivirus donor construct is an integrase deficient lentiviral vector (IDLV). IDLVs may be produced as described, for example using lentivirus vectors that include one or more mutations in the native lentivirus integrase gene, for instance as disclosed in Leavitt et al. (1996) *J. Virol.* 70(2):721-728; Philippe et al. (2006) *Proc. Nat'l Acad. Sci. USA* 103(47):17684-17689; and WO 06/010834. In certain embodiments, the IDLV is an HIV lentiviral vector comprising a mutation at position 64 of the integrase protein (D64V), as described in Leavitt et al. (1996) *J. Virol.* 70(2):721-728.

The donor polynucleotides described herein may also comprise one or more positive and/or negative selection or screening markers. Positive selection markers are those polynucleotides that encode a product that enables only cells that carry and express the gene to survive and/or grow under certain conditions. For example, cells that express neomycin resistance ($Neo^R$) gene are resistant to the compound G418, while cells that do not express $Neo^R$ are killed by G418. Other examples of positive selection markers including hygromycin resistance, Zeocin™ resistance and the like will be known to those of skill in the art. Negative selection markers are those polynucleotides that encode a produce that enables only cells that carry and express the gene to be killed under certain conditions. For example, cells that express thymidine kinase (e.g., herpes simplex virus thymidine kinase, HSV-TK) are killed when gancyclovir is added. Other negative selection markers are known to those skilled in the art. Screening markers that may be used can be, for example, GFP or beta-galactosidase. Other screening markers may include sequences encoding polypeptides that will be expressed on the cell surface, allowing for identification with specific antibodies or other ligands to that surface expressed polypeptide. The antibodies or ligands in these assays may be tagged in some manner, for example with a fluorophore, to allow rapid cell screening.

As described herein, when cells are transduced with Ad5/35 ZFN construct and IDLV donor construct, two major homologous recombination (HR) based target integration (TI) events occur: single gene target insertion and lentiviral 2-LTR circle based multiple copy gene insertion. Lentiviral LTR based end joining (LTR-EJ) and lentiviral genome random integration also occur at a very low efficiency. Single gene targeted insertion is useful for gene correction, gene disruption and gene knock-in. Multiple copy gene insertion into a designated genomic locus is important for the over expression of beneficial genes in a gene therapy setting and for engineering cell lines for biotechnology applications (e.g. enhanced protein production).

Lentivital construct I (FIG. 1A) is designed to selectively enrich either single gene target insertion or multiple copy gene insertion via a single positive/negative selection or screening marker. See, FIG. 2A. As noted above, any selection or screening marker can be used. In certain embodiments, the selection marker can be both a positive and negative selection marker, for example, a hyg-TK fusion gene that can be used for both positive and negative selection.

When the single selection marker is a negative selection marker (FIG. 2B), cells with single copies can be selected for by killing cells that have undergone 2-LTR. Also, the use of a negative selection marker can select out cells that have undergone random integration of the lentivirus vector or have the vector integrated via NHEJ. Thus, the surviving population after negative selection are mainly be cells that have HDR-driven single copy insert into the double stranded break induced by the nuclease at one or both alleles. In the case of positive selection (hygromycin) cells that have undergone the insertion of a 2-LTR circle survive the selection process (FIG. 2C).

The inclusion of positive or negative selection markers in the donor construct allows for controlled selection of targeted integration events. A negative selection marker allows for the controlled targeted integration of single copy of the gene of interest (on one or more both alleles) and allows for the removal of multiple copy, random integrants, or integration via NHEJ. Use of positive selection marker allows for the selection of targeted integration of multiple copies of the donor construct. As noted above, the selection marker can be a dual marker (e.g. hyg-TK fusion) to allow for selection of either outcome using a single vector construct.

The inclusion of one or more screening markers similarly allows for the controlled identification of targeted integration events. In addition, one or more screening markers can be used in combination with negative or positive selection markers to allow for removal of multiple integration events, random integrations or integration via NHEJ.

Lentiviral construct II (FIG. 1B) shows another exemplary donor lentiviral vector comprising two selection or screening markers. Typically, the selection or screening marker inside the homology arms (selection/screening marker 1) is promoterless such that it is only expressed when integrated into the genome at the targeted site. A downstream active gene is also included and is preferably expressed using either a direction fusion and/or a splice acceptor (SA), internal ribosome entry site (IRES), or 2A self-cleaving peptide. Therefore, precise site-specific insertion is required for expression of selection marker 1 and, accordingly, this marker can be used selectively remove random integrants and cells with insertion of the lentiviral construct via NHEJ.

The second selection or screening marker (selection/screening marker 2) is typically outside the homology arms and is preferably operably linked to a control element (e.g., promoter) that drives its expression. Combining selection for selection markers 1 and 2 allows for selection of cell populations with multiple copies of the donor inserted via homology-direct repair at the target site can be selected for in a single step with both marker selected for at one or both alleles. For example, constructs comprising a positive selection marker 1 and a negative selection marker 2 allow for selection of cells having primarily a site-specifically integrated single copy of the gene of interest (FIG. 3C). Constructs comprising a negative selection marker 1 and a position selection marker 2 allow for selection of cells having primarily site-specifically integrated multiple copies of the gene of interest (FIG. 3D). Constructs in which both selection marker 1 and selection marker 2 are positive selection markers allows for selection of cells with site-specifically integrated single or multiple copies of the gene of interest.

Lentiviral constructs IV and V (FIG. 4 and FIG. 5) allow for enrichment of cells containing a single copy of the transgene of interest that has been site-specifically inserted into the target genome via HR-TI. Rarely, selection or screening for integration of these constructs will result in cells containing multiple copies of the transgene. However, cells selected using these designs do not contain randomly integrated constructs and/or constructs integrated via LTR-EJ. The design designated "lentiviral construct V" integrates the smallest lentiviral sequence into the genome.

Delivery

The ZFNs described herein may be delivered to a target cell by any suitable means. Methods of delivering proteins comprising zinc fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

ZFNs as described herein may also be delivered using vectors containing sequences encoding one or more ZFNs. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties.

In certain embodiments, the vector is an adenovirus vector. Thus, described herein are adenovirus (Ad) vectors for introducing heterologous sequences (e.g., zinc finger nucleases (ZFNs)) into cells.

Non-limiting examples of Ad vectors that can be used in the present application include recombinant (such as E1-deleted), conditionally replication competent (such as oncolytic) and/or replication competent Ad vectors derived from human or non-human serotypes (e.g., Ad5, Ad11, Ad35, or porcine adenovirus-3); and/or chimeric Ad vectors (such as Ad5/35) or tropism-altered Ad vectors with engineered fiber (e.g., knob or shaft) proteins (such as peptide insertions within the HI loop of the knob protein). Also useful are "gutless" Ad vectors, e.g., an Ad vector in which all adenovirus genes have been removed, to reduce immunogenicity and to increase the size of the DNA payload. This allows, for example, simultaneous delivery of sequences encoding ZFNs and a donor sequence. Such gutless vectors are especially useful when the donor sequences include large transgenes to be integrated via targeted integration.

Replication-deficient recombinant adenoviral vectors (Ad) can be produced at high titer, and they readily infect a number of different cell types. Most adenovirus vectors are engineered such that a transgene replaces the Ad E1a, E1b, and/or E3 genes; subsequently the replication defective vector is propagated in cells that provide one or more of the deleted gene functions in trans. For example, human 293 cells supply E1 function. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083-1089 (1998)).

Additional examples of the use of adenovirus vectors for gene transfer in clinical trials include Rosenecker et al., Infection 24:1 5-10 (1996); Welsh et al., Hum. Gene Ther. 2:205-18 (1995); Alvarez et al., Hum. Gene Ther. 5:597-613 (1997); Topf et al., Gene Ther. 5:507-513 (1998).

In certain embodiments, the Ad vector is a chimeric adenovirus vector, containing sequences from two or more different adenovirus genomes. For example, the Ad vector can be an Ad5/35 vector. Ad5/35 is created by replacing one or more of the fiber protein genes (knob, shaft, tail, penton) of Ad5 with the corresponding fiber protein gene from a B group adenovirus such as, for example, Ad35. The Ad5/35 vector and characteristics of this vector are described, for example, in Ni et al. (2005) "Evaluation of biodistribution and safety of adenovirus vectors containing group B fibers after intravenous injection into baboons," Hum Gene Ther 16:664-677; Nilsson et al. (2004) "Functionally distinct subpopulations of cord blood CD34+ cells are transduced by adenoviral vectors with serotype 5 or 35 tropism," Mol Ther 9:377-388; Nilsson et al. (2004) "Development of an adenoviral vector system with adenovirus serotype 35 tropism; efficient transient gene transfer into primary malignant hematopoietic cells," J Gene Med 6:631-641; Schroers et al. (2004) "Gene transfer into human T lymphocytes and natural killer cells by Ad5/F35 chimeric adenoviral vectors," Exp Hematol 32:536-546; Seshidhar et al. (2003) "Development of adenovirus serotype 35 as a gene transfer vector," Virology 311:384-393; Shayakhmetov et al. (2000) "Efficient gene transfer into human CD34(+) cells by a retargeted adenovirus vector," J Virol 74:2567-2583; and Sova et al. (2004), "A tumor-targeted and conditionally replicating oncolytic adenovirus vector expressing TRAIL for treatment of liver metastases," Mol Ther 9:496-509.

As noted above, ZFNs and polynucleotides encoding these ZFNs may be delivered to any target cell.

Applications

The disclosed methods and compositions allow for a rapid and controlled generation of cells having a single or multiple transgenes integrated into a specific site in the genome, depending on the desired level of transgene expression. Controlled integration of the number of transgenes has both therapeutic and non-therapeutic (e.g. basic science research, biotechnology applications, cell engineering) applications. Single gene targeted insertion is useful for gene correction, gene disruption and gene knock-in. Multiple copy gene insertion into a designated genomic locus is important for the over expression of beneficial genes in a gene therapy setting and for engineering cell lines for biotechnology applications (e.g. enhanced protein production).

The ability to control the number of transgenes that are site-specifically integrated into a genome overcomes problems associated with insertional mutagenesis or variegated transgene expression caused by position effects. In addition, the selection process is more rapid than what is required for standard amplification procedures and is less prone to causing chromosomal abnormalities.

Thus, the compositions and methods described herein can be used for controlled targeted integration, gene modification, gene correction, and gene disruption. The compositions (e.g., lentiviral-ZFN vectors) and methods described herein can also be used for the production of protein and/or in the treatment of various genetic diseases and/or infectious diseases.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting.

EXAMPLES

Example 1

Vector Construction and Selection of Cells with Single or Multiple Integrated Transgenes A lentiviral vector as shown in FIG. 1C was produced as essentially as described in Follenzi, A. & Naldini, L. (2002) *Methods Enzymol.* 346:454-465. Homology-arms (left and right) are homologous to CCR5 and flank a sequence encoding GFP. The CCR5-GFP construct was designated CCR-LVGFP. Briefly, 293T cells were cotransfected by calcium phosphate precipitation with the required transfer vector plasmid, the pMD.Lg/pRRE.D64VInt packaging plasmid, the pMD2.VSV-G envelope-encoding plasmid, and pRSV-Rev. Vector particles were purified over a DEAE-sepharose column and then concentrated by ultracentrifugation. The infectious titer was determined using a quantitative PCR method. Lentiviral vectors as shown in FIGS. 1A, 1B, 1D and 1E are also constructed.

The vectors shown in FIGS. 1A, 1B, 1D and 1E are used in combination with ZFNs to select for single or multiple integrated transgenes as follows. When target cells are transduced with Ad5/35 ZFN virus and non-integrated lentiviral donor virus (FIGS. 1A-C), two major homologues recombination (HR)-based target integration (TI) events occur: single gene target insertion and lentiviral 2-LTR circle based multiple copy gene insertion. Lentiviral LTR based end joining (LTR-EJ) and lentiviral genome random integration also occur at a very low efficiency.

Lentiviral construct I (FIG. 1A) selectively enriches either single gene target insertion or multiple copy gene insertion via a positive or negative selection marker. The outcomes that can be selected for using this lentiviral donor construct are outlined in FIGS. 2A and B. Briefly, the selection marker used could be the hyg-TK fusion gene that can be used for both positive and negative selection. In the case of positive selection (e.g., hygromycin), this selects for cells that have undergone the insertion of a 2-LTR circle, and, at much lower frequencies, cells with randomly integrated vector, cells with vector that is integrated at one end via homologous recombination and at the other via non-homologous end-joining (HR-EJ) and cells with end-joining of the LTRs (LTR-EJ). Construct 1 can also be sued with a screening marker to screen for insertion events.

A negative selection marker (e.g. TK) in this construct selects out those cells that have undergone 2-LTR circle and leave the single TI events intact. However, unmodified cells are also selected. Also, the negative selection marker can select out cells that have undergone random integration of the lentivirus vector or have the vector integrated via NHEJ or both HR/NHEJ.

Use of a positive or negative selection marker allows for control, in a single step, of targeted gene addition as a single gene insert and allows for the removal of multiple copy, random integrants, or integration via NHEJ or HR/NHEJ. Alternatively, multiple copy insertion can be selected for using a positive selection marker. As noted herein, the selection marker can be a dual marker (e.g. hyg-TK fusion) to allow for selection of either outcome using a single vector construct.

However, lentiviral construct I does not selective out random integrants or integration via NHEJ of HE/NHEJ by positive selection. In cases where elimination of these integrants is desired, lentiviral construct II can be used. Lentiviral construct II includes a second positive selection marker that is promoterless and requires the precise insertion of this marker downstream of an active gene to be expressed and typically inside the homology arms. Expression of this promoterless selection marker from an endogenous promoter can be achieved by directly fusing it in-frame to the native gene at the break site, through the use of a splice acceptor (SA) and its insertion into an intron, or through an internal ribosome entry site (IRES) or 2A peptide. This would require precise site-specific insertion for this positive selection marker to be expressed, and therefore, this marker could selectively remove random integrants and cells with insertion of the lentiviral construct via NHEJ or HR/NHEJ. Construct II can also be used with a promoterless screening marker wherein expression of the screening marker is dependent upon an endogenous promoter following direct in-frame fusing to the native gene.

Lentiviral construct II allows for selection of cells having a single copy of the transgene or multiple (e.g., 2, 3, 4, or even more) copies of the transgene. For example, when selection marker 1 is a positive selection marker, selection of cells transduced with ZFNs and Lentiviral construct II will produce cells with single copy of the transgene, either by HR-TI, or, at very low efficiency, via HR-EJ (FIG. 3A). When selection marker 2 is a positive selection marker (as with lentiviral construct I), selected cells with include multiple copies of the transgene inserted via HR-TI, as well as cells into which the transgene is randomly integrated or integrated via LTR-EJ or HR-EJ (FIG. 3B). When selection marker 1 is a positive selection marker and selection marker 2 is negative selection marker, positive and negative selection will give rise to cells containing a single HR-TI copy of the transgene, without multiple copy HR-TI, random integration and/or LTR-EJ. Use of a positive selection marker for selection marker 2 and a negative selection marker for selection marker 1 allows for the selection of cells containing multiple HR-TI copies of the transgene and without a single HR-TI copy of the transgene. Use of a positive selection marker for both selection markers 1 and 2 allows for selection of cells with both multiple copy HR-TI (head to tail) and single copy HR-TI.

Use of a positive selection marker in lentiviral constructs IV and V allows for selection of cells that are highly enriched in cells containing a single copy of transgene, integrated via homologous recombination to the targeted site (HR-TI). See, FIG. 4 and FIG. 5. The selected cells populations may contain cells with multiple copies of the transgene, but the selected cell populations will not contain randomly integrated transgene(s) or transgene(s) integrated by LTR end joining (LTR-EJ). Constructs IV and V and also be used with screening markers.

Therefore; using these different selection strategies, cell populations that are enriched for a certain type of integration event are rapidly selected. Additionally, populations can also be screening using screening technologies.

Example 2

Targeted Integration of a Single Copy or Multiple Copies of a Transgene

The lentiviral donor construct designated CCR-LVGFP as described in Example 1 was transduced into K562, Hep3B and human mesenchymal stem cells (hMSCs) cells in the presence of Ad5/35 ZFNs targeted to CCR5. See, U.S. Pat. No. 7,951,925 for a complete description of the CCR5 Ad5/35 ZFNs.

As shown in FIG. 6, co-transduction in K562 cells resulted in cells having a single copy of GFP on one (heterozygous) or both (homozygous) alleles as well as heterozygous and homozygous cells having multiple copies of GFP. In addition, cells in which one or more copies of the construct were integrated by end-joining of the LTRs were also generated.

Figure 7:
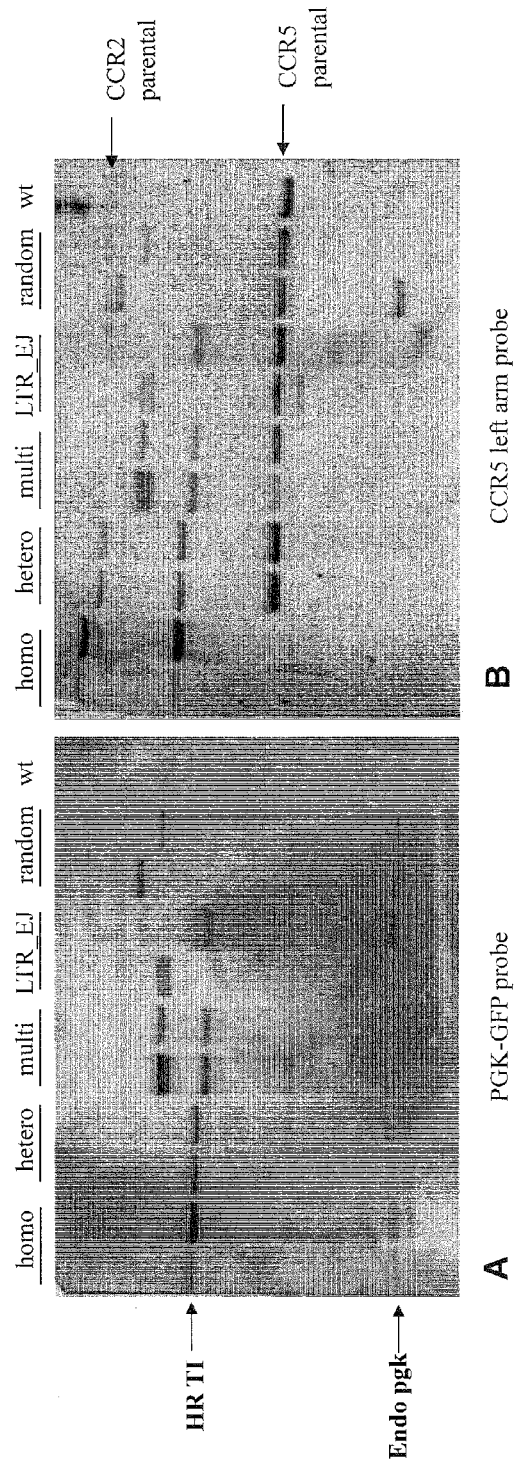
FIG. 7, panels A and B, show Southern blot analysis of selected individual cell clones shown in FIG. 4. The type of selected clone is indicated above each lane.
Figure 8:
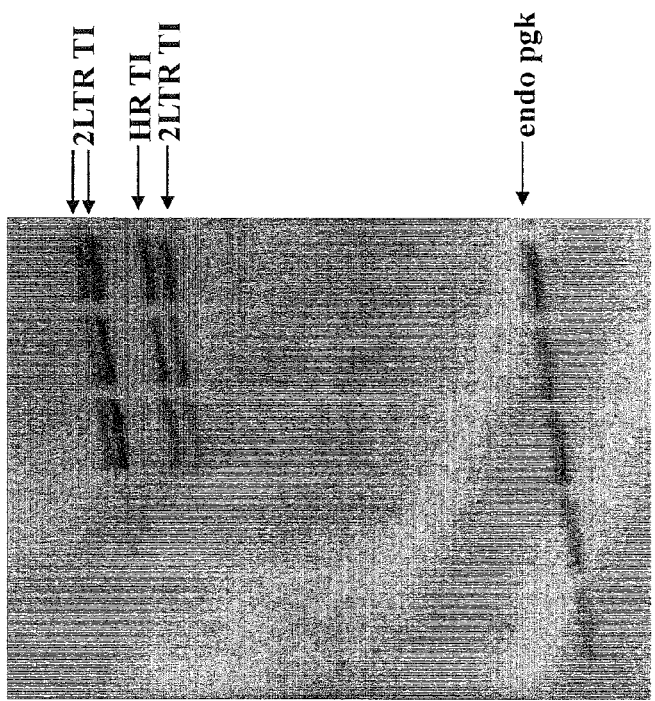
FIG. 8 shows Southern blot analysis of pools of cells shown in FIG. 6 using a pgf-eGFP probe.

Selected clones from each of the types of integration events as well as pools of K562 cells shown in FIG. 6 were also analyzed by Southern blot analysis. In particular, cellular DNA of selected clones was probed with either PGK-GFP (FIG. 7A) or CCR5 left homology arm probe (FIG. 7B). Results of Southern blot analysis on pools of cells using a pgf-eGFP probe are shown in FIG. 8.

Figure 9:
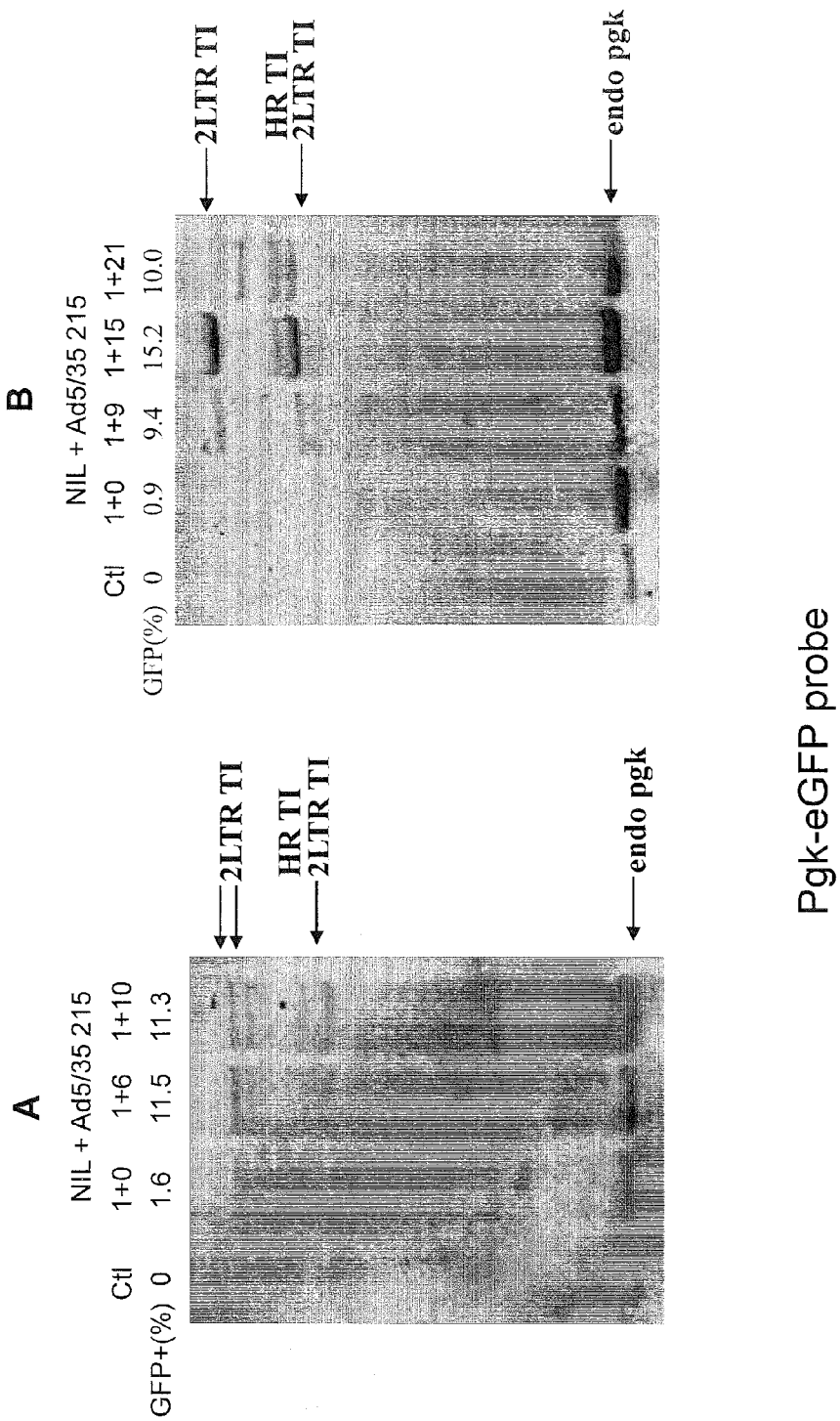
FIG. 9, panels A and B, show Southern blot analysis of Hep3B cells (FIG. 9A) and human mesenchymal stem cells (hMSCs, FIG. 9B) comprising the GFP donor construct and Ad5/35 ZFNs described in FIG. 6.

Similarly, Southern blot analysis of Hep3B cells (FIG. 9A) and human mesenchymal stem cells (hMSCs, FIG. 9B) shows single and multiple HR-TI events.

Figure 10:
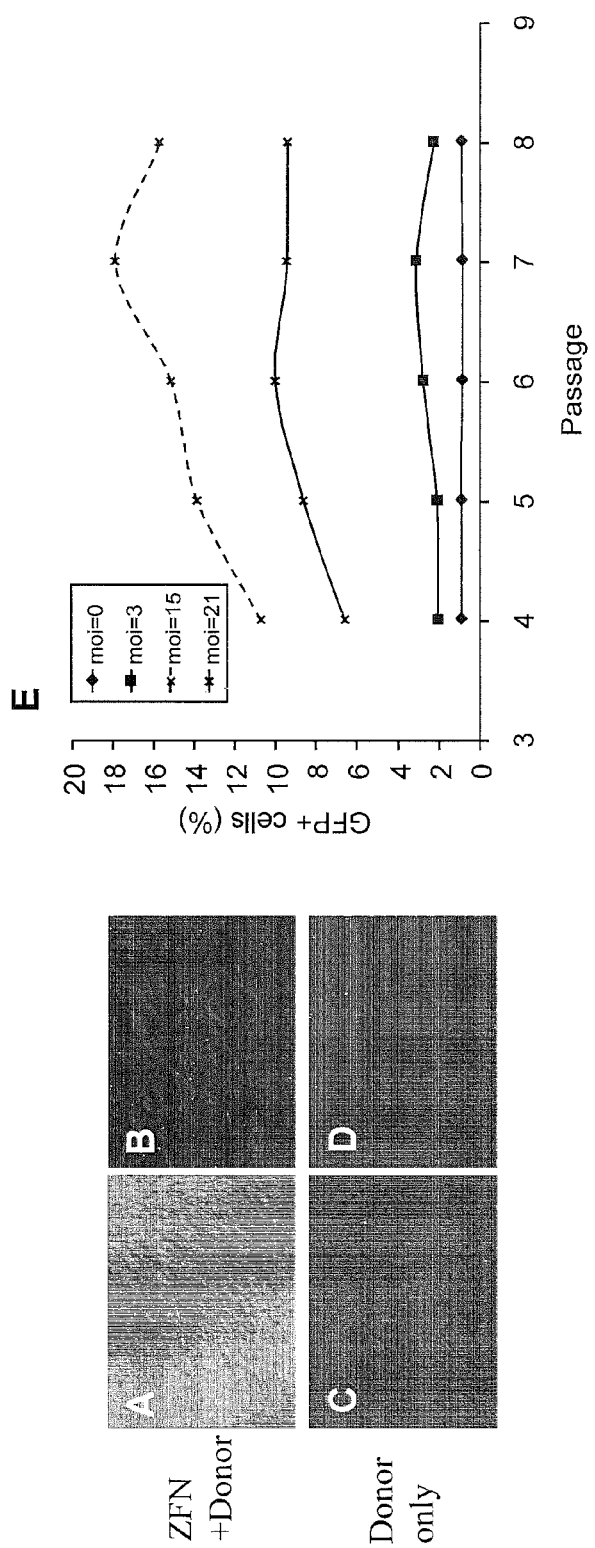
FIG. 10, panels A to E, show GFP expression is stable over cell passages in hMSCs comprising ZFNs and lentiviral GFP donor constructs.

Expression of GFP over time (cell passages) was also evaluated in hMSCs. Cells were transduced with CCR-LVGFP alone or Ad5/35 CCR5-ZFNs and CCR-LVGFP at mois 0, 3, 15 and 21. FIG. 10, panels A to E, show GFP expression is stable over cell passages in hMSCs comprising ZFNs and lentiviral GFP donor constructs.

Cells comprising integrated GFP were also evaluated for adipogenesis and osteogenesis. Briefly, hMSCs were seeded in poly-L-lysine coated 24 well plates (2 million/plate for osteocyte differentiation, 4 million/plate for adipocyte differentiation). On the 2nd day, the cells were thoroughly washed with differentiation basal media (10% ES-FBS, 1% PSG in DMEM) and the induction media added to the cells. The osteogenic induction media comprised basal media plus 0.05 mM ascorbic acid-2-phosphate, 0.1 uM dexamethasone, 10 mM β-glycerophosphate. The adipogenic induction media comprised basal media plus 1 uM Dex, 100 ug/ml IBMX, 10 ug/ml insulin and 5 uM Troglitazone. Cells were incubated with in induction media for about 10-14 days, with media replaced by fresh media every 2-3 days.

For staining, the cells were washed with PBS for 3 times, fixed in 10% formalin for 20 minutes and washed 2 times with PBS washing. For osteocyte staining, the cells were stained with Sigma Alkaline Phosphatase staining Kit. For adipocyte staining, the cells were further washed with propylene glycol for 5 minutes, then stained with Oil Red O in propylene glycol for 2 hours. After staining, the cells were washed with 85% propylene glycol for 5 minutes, rinsed with water for 3 times and preserved in 50% glycerol.

Figure 11:
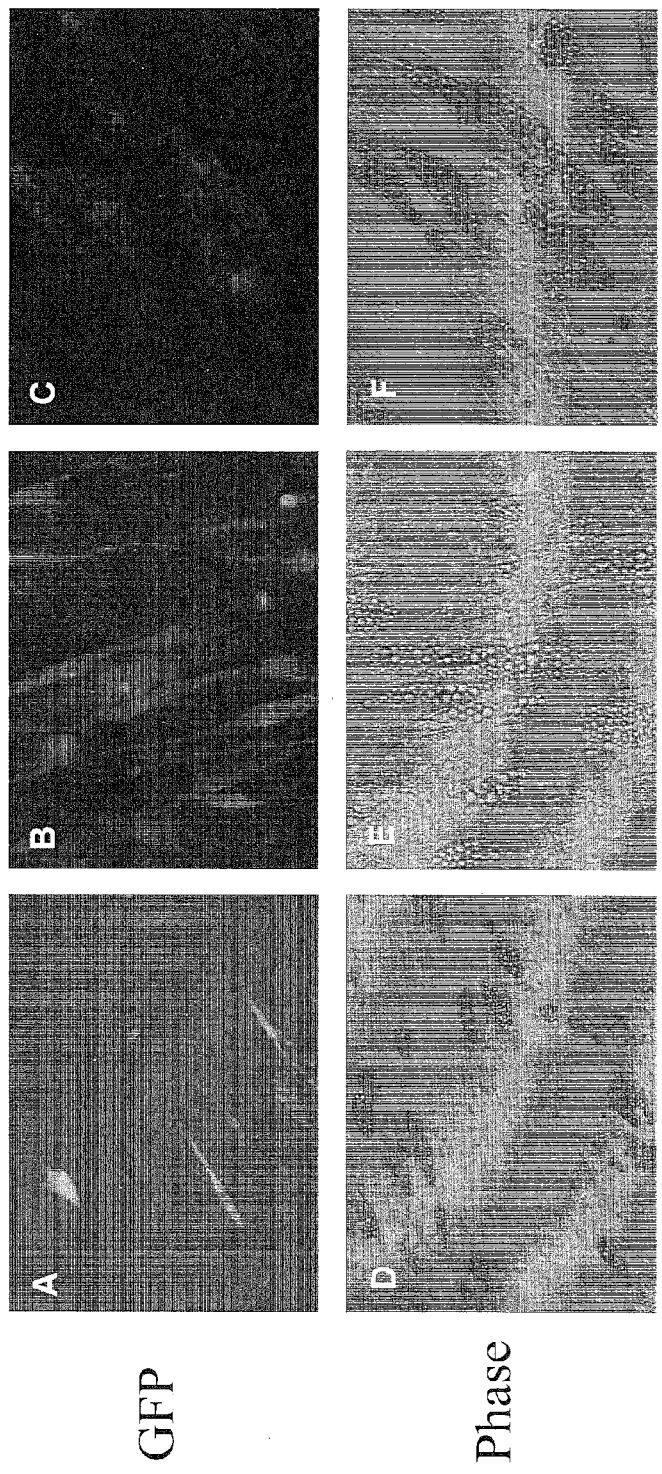
FIG. 11, panels A to F, show that hMSCs cells into which the GFP construct has been integrated continue to express GFP after differentiation into adipocytes.
Figure 12:
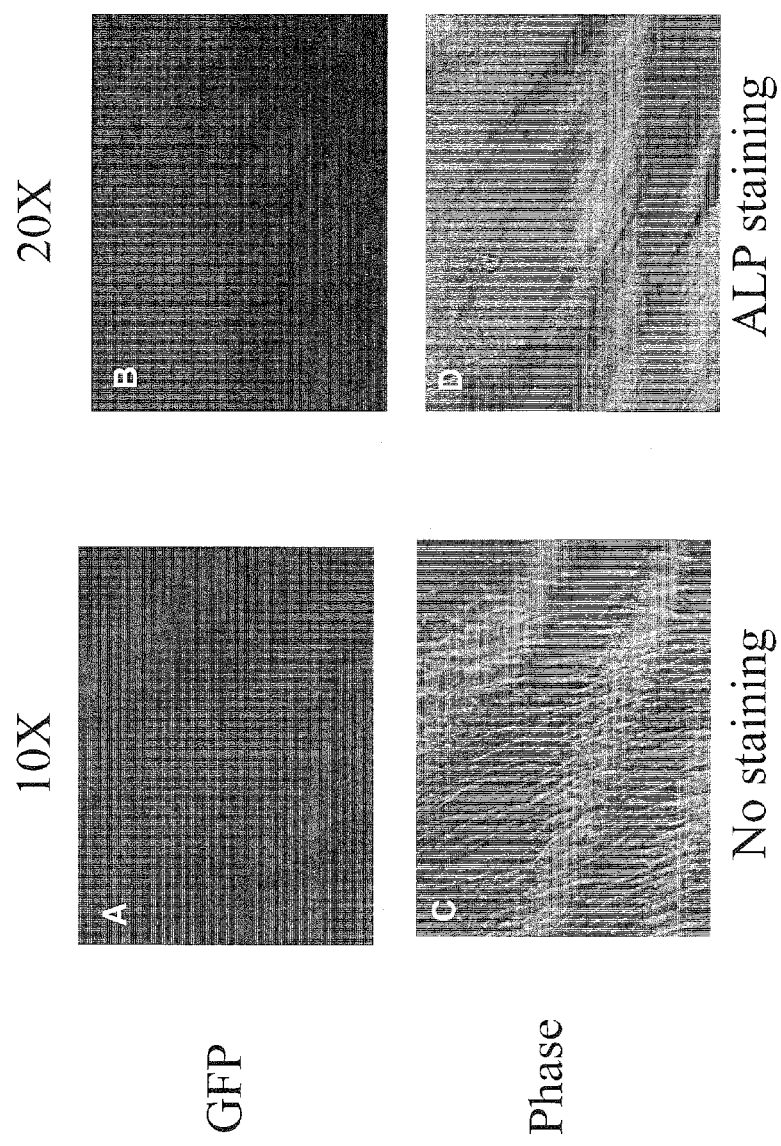
FIG. 12, panels A to D, show that hMSCs cells into which the GFP construct has been integrated continue to express GFP after osteogenic differentiation.

As shown in FIGS. 11 and 12, hMSCs cells into which the GFP construct has been integrated continue to express GFP after adipogenesis and osteogenesis.

What is claimed is:

1. An integrase-defective lentiviral (IDLV) donor polynucleotide comprising, between the lentivirus LTRs,
  a gene of interest and first and second nucleotide sequences that are homologous sequences to a region of interest of endogenous cellular chromatin of a mammalian cell, wherein the homologous sequences are identical to endogenous cellular chromatin sequences of the mammalian cell; and further wherein the donor polynucleotide is selected from the group consisting of:
  (i) a donor polynucleotide comprising the gene of interest flanked by the first and second homologous sequences and a selectable marker outside the first and second homologous sequences;
  (ii) a donor polynucleotide comprising the gene of interest, a first selectable marker, and a second selectable marker, wherein the gene or interest and the first selectable marker are flanked by the first and second homologous sequences and further wherein the second selectable marker is outside the first and second homologous sequences;
  (iii) a donor polynucleotide comprising the gene of interest and a selectable marker, wherein the gene of interest and the selectable marker are outside the first and second homologous sequences; and
  (iv) a donor polynucleotide comprising the gene of interest and a selectable marker, wherein the gene of interest and the selectable marker are flanked by the first and second homologous sequences.

2. The IDLV donor polynucleotide of claim 1, wherein the first or second selectable marker is a positive selection marker.

3. The IDLV donor polynucleotide of claim 1, wherein the first or second selectable marker is a negative selection marker.

4. The IDLV donor polynucleotide of claim 1, wherein the first selectable marker is a positive selection marker and the second selectable marker is a negative selection marker.

5. The IDLV donor polynucleotide of claim 4, wherein the positive-negative selection marker is hyg-TK.

6. The IDLY donor polynucleotide of claim 1, wherein the cell is a human cell.

7. The DLV donor polynucleotide of claim 1, wherein the first and second nucleotides flank the exogenous sequence.

8. A method for controlled, site-specific integration of a single copy or multiple copies of an exogenous nucleic acid sequence into a cell, the method comprising:
   (a) expressing a first fusion protein in the cell, the first fusion protein comprising a first zinc finger binding domain and a first cleavage half-domain, wherein the first zinc finger binding domain has been engineered to bind to a first target site in a region of interest in the genome of the cell;
   (b) expressing a second fusion protein in the cell, the second fusion protein comprising a second zinc finger binding domain and a second cleavage half domain, wherein the second zinc finger binding domain binds to a second target site in the region of interest in the genome of the cell, wherein the second target site is different from the first target site; and
   (c) contacting the cell with any of the IDLV donor polynucleotides of claim 1;
   wherein binding of the first fusion protein to the first target site, and binding of the second fusion protein to the second target site, positions the cleavage half-domains such that the genome of the cell is cleaved in the region of interest, thereby resulting in integration of one or more copies of the exogenous sequence into the genome of the cell in the region of interest.

9. The method according to claim 8, wherein the exogenous nucleic acid sequence comprises a cDNA.

10. The method of claim 8, wherein the region of interest is in a region of the genome that is not essential for viability.

11. The method of any claim 8, wherein the region of interest is in a region of the genome that is transcriptionally active.

12. The method of claim 8, wherein a single copy of the exogenous sequence is integrated into the genome of the cell.

13. The method of claim 8, wherein multiple copies of the exogenous sequence are integrated into the genome of the cell.

14. The method according to claim 8, wherein at least one of the fusion proteins comprises an alteration in the amino acid sequence of the dimerization interface of the cleavage half-domain.

15. The method according to claim 8, wherein the cell is a mammalian cell.

16. The method according to 15, wherein the cell is a human cell.

* * * * *